(12) United States Patent
Cong et al.

(10) Patent No.: US 8,241,634 B2
(45) Date of Patent: Aug. 14, 2012

(54) CARBON SUPPLY DEVICE FOR CULTIVATING MICRO-ALGAE IN LARGE SCALE AND ITS APPLICATION METHOD AND USE

(75) Inventors: Wei Cong, Beijing (CN); Zhenfeng Su, Beijing (CN); Ruijuan Kang, Beijing (CN); Chengyan Yang, Beijing (CN); Zhaoling Cai, Beijing (CN)

(73) Assignee: Institute of Process Engineering, Chinese Academy of Sciences, Beijing (CN)

( * ) Notice: Subject to any disclaimer, the term of this patent is extended or adjusted under 35 U.S.C. 154(b) by 1043 days.

(21) Appl. No.: 12/096,853

(22) PCT Filed: Dec. 11, 2006

(86) PCT No.: PCT/CN2006/003357
§ 371 (c)(1),
(2), (4) Date: Aug. 6, 2008

(87) PCT Pub. No.: WO2007/068191
PCT Pub. Date: Jun. 21, 2007

(65) Prior Publication Data
US 2008/0311646 A1 Dec. 18, 2008

(51) Int. Cl.
*A01N 65/00* (2009.01)
*A61K 36/02* (2006.01)
*C12N 1/12* (2006.01)
*C12M 1/00* (2006.01)
*C12M 3/00* (2006.01)

(52) U.S. Cl. .............. 424/195.17; 435/257.1; 435/303.1

(58) Field of Classification Search .................. None
See application file for complete search history.

(56) References Cited

U.S. PATENT DOCUMENTS

| 4,724,214 A | * | 2/1988 | Mori | .............. 435/292.1 |
| 5,162,051 A | * | 11/1992 | Hoeksema | ............... 47/1.4 |
| 5,981,271 A | | 11/1999 | Doucha et al. | |

FOREIGN PATENT DOCUMENTS

| CN | 2302258 Y | 12/1998 |
| CN | 14723056 A | 2/2004 |
| CN | 200410009360.4 A | 7/2004 |
| JP | 7246086 A | 9/1995 |
| JP | 8173139 A | 7/1996 |
| JP | 2000139444 A | 5/2000 |
| JP | 2001269161 A | 10/2001 |

OTHER PUBLICATIONS

Tsuge, et al. (2004) Liquid Circulation and Mass Transfer in an External-Loop Airlift Reactor with Partitioning Plates. J. Chem. Eng. of Japan. vol. 37, No. 8, pp. 941-946.*
Meng, et al. (2005) Liquid Circulation Flow in a Rectangular Airlift Bubble Column. J. Chem. Eng. of Japan, vol. 38, No. 12, pp. 1015-1019.*
Chen et al. (1991) Int. J. Heat Mass Transfer. vol. 34, No. 1, pp. 237-246.*
Chaumont, Daniel, "Biotechnology of algal biomass production: a review of systems for outdoor mass culture", J. Applied Phycology 5:593-604, 1993 (Belgium: Kluwer Academic Publishers).
Richmond, Amos, "Large scale microalgal culture and applications", Progress in Phycological Research, vol. 7 (Round/Chapman, eds.), Biopress Ltd. 1990.
Borowitzka, L. J., "Development of Western Biotechnology's Algal β-Carotene Plant", Bioresource Technology 38, pp. 251-252, 1991.
Hu, Qiang & Amos Richmond, "Optimizing the population density in *Isochrysis galbana* grown outdoors in a glass column photobioreactor", J. Applied Phycology 6:391-396, 1994 (Belgium: Kluwer Academic Publishers).
Carlozzi, P. and Torzillo, G., "Productivity of *Spirulina* in a strongly curved outdoor tubular photobioreactor", Appl. Microbiol. Biotechnol. 45:18-23, 1996.
Lee, Yuan-Kun et al., "Design and Performance of an α-type tubular photobioreactor for mass cultivation of microalgae", J. Applied Phycology 7:47-51, 1995 (Belgium: Kluwer Academic Publishers).
Hu, Qiang, Hugo Guterman and Amos Richmond, "A Flat Inclined Modular Photobioreactor for Outdoor Mass Cultivation of Photoautotrophs", Biotechnology and Bioengineering, vol. 51, pp. 51-60, 1996 (John Wiley & Sons, Inc.).
Wohlgeschaffen, Gary D., D. V. Subba Rao & Ken H. Mann, "Vat incubator with immersion core illumination—a new, inexpensive setup for mass phytoplankton culture", J. Applied Phycology 4:25-29, 1992 (Belgium: Kluwer Academic Publishers).
Xu, Bo and Wang, Changhai "High Density Culture of Microalgal Cells in Flat Plate Photobioreactor" Food and Fermantation Industries, vol. 29, No. 1, 2003 (pp. 36-40).
Tian, Zhili and Wang, Changhai "Cultivation of *Chaetoceros gracilis* in Airlift Photobioreator" Marine Science Bulletin, vol. 24, No. 1, Feb. 2005 (pp. 35-40).

* cited by examiner

*Primary Examiner* — Chris R Tate
*Assistant Examiner* — Russell Fiebig
(74) *Attorney, Agent, or Firm* — Volpe and Koenig, P.C.

(57) ABSTRACT

Disclosed herein is a carbon supply device for supplying carbon dioxide during large scale cultivation of micro-algae in open pond, and its application method and use. The device comprises a trap container in which a partition plate is installed vertically and has a 10-50 cm gap from the container bottom, and the partition plate is higher than the wall of the trap container; and a gas distributor is positioned at the bottom of the container. In use, the trap carbon supply device is embedded in bottom of an open pond, wherein the partition plate is above the liquid level of the culture solution in the open pond such that the culture solution driven by a stirrer flows into the trap carbon supply device from one side thereof, and flows out of the device from the other side thereof, wherein the culture solution is mixed with carbon dioxide at the bottom of the container.

20 Claims, 3 Drawing Sheets

Relationship between distribution of three inorganic carbon forms in water vs pH

CARBON SUPPLY DEVICE FOR CULTIVATING MICRO-ALGAE IN LARGE SCALE AND ITS APPLICATION METHOD AND USE

FIELD OF INVENTION

The present invention belongs to the field of large scale cultivation of micro-algae, and particularly relates to a carbon supply device for high efficient carbon dioxide supplying, its application method and use on large scale cultivation of micro-algae in an open pond.

BACKGROUND

Cells of micro-algae are rich in various bioactivity substances such as proteins, amino acids, carbohydrates, vitamins, antibiotics, highly unsaturated fatty acids, polysaccharides, and colorants. This makes micro-algae great resources with high economic value. Some micro-algae possess abilities to produce hydrocarbon (such as *Botryococcus braunii*), and thus have promising application in field of renewable energy production. Today, as global food and energy crises are becoming more severe, development and utilization of micro-algal resource have exhibited a great significance and economic prospect. Large scale cultivation of micro-algae is normally carried out either in open cultivation systems or in the closed photoreactors. The open cultivation system comprises open-pond, raceway pond, or round shallow pond. It has been successfully applied in the commercial production of *Spirulina, Chlorella*, and *Dunaliella salina* due to its simple management and low investment. (Chaumont D., J. Appl. Phycol., 1993, 5:59-604; Bonnin G., *Spirulina* Production Engineering Handbook, BECCMA ed., Nantes, France, 1992, 140-159; Richmond A., Progress in Physiological Research, Vol. 7, Biopress, Bristol., 1990, 269-330; Borowitzka L. T., Bioresource Technology, 1991, 38:251-252). The closed photobioreactors have different structures, such as airlift reactor, stirred reactor, or tubular reactor, which can be used for producing high value added products (such as medicinal or health products) or used as seed tank for open-pond cultivation (Hu Q., J. Appl. Phycol., 1994, 6:391-396; Carlozzi P., Appl. Microbiol. Biotecnol., 1996, 45:18-23; Lee Y. K., J. Appl. Phycol., 1995, 7(1):45-52; Hu Q., Biotech. Bioeng., 1996, 51(1):51-60; Wohlgeschaffen G. D., J. Appl. Phycol., 1992, 4:25-29).

Micro-algal cells fix carbon dioxide through photosynthesis and carbon comprised more than half of its dry weight. Therefore sufficient carbon source is needed during micro-algae cultivation. Carbon dioxide exists in the form of $HCO_3^-$, $CO_3^{2-}$ and free $CO_2$ in the solution. The ratios of the three carbonate forms vary with the pH value. The detail is shown in FIG. 6.

In large scale open cultivation conditions, the depth of the culture solution is usually kept less than 15-20 cm to insure the sufficient light irradiation for cell growth. In this case, if $CO_2$-containing gas is directly introduced into the culture solution for supplying carbon, the residence time of bubbles in the culture solution is short due to shallow depth of the solution, and the utilization of $CO_2$ is low. For this reason, $NaHCO_3$ is currently the major carbon source used in large scale micro-algae cultivation. But $NaHCO_3$ can not be fully utilized as carbon source during the cultivation. The dissociation and utilization of the $HCO_3^-$ lead to a continual rise of pH value and unsuitable for micro-algae growth. More than half of the $NaHCO_3$ is turned into unusable $Na_2CO_3$ and therefore results in a considerable waste of water and carbon source. This is one of the main reasons for the high cost of micro-algae production. For example, the consumption for producing one ton of *Spirulina* (based on dry weight) is 8 tons of $NaHCO_3$, 1000 tons of water and 3 tons of nutrient salts.

As analyzed above, the cost of algal cultivation can be reduced dramatically by the direct use of $CO_2$ gas or liquid only if the utilization is greatly improved. According to the estimate, for *Spirulina* production, the cost of carbon source by using $NaHCO_3$ is 6 times of that by using $CO_2$ for carbon supply (estimate is based on the assumption that all the provided $CO_2$ is completely absorbed by the culture solution). Additionally, $CO_2$ is the optimal carbon source for micro-algae growth. The pH value of the culture solution is kept relatively constant by using $CO_2$, which is beneficial for maintaining desirable culture environment, and allows water to be used repeatedly or for an extended period.

SUMMARY

One purpose of the present invention is to overcome the difficult problems in direct using $CO_2$ in open cultivation due to the extremely low absorption of $CO_2$, and to provide an efficient carbon supply device to make it economically feasible to use $CO_2$ as carbon source in micro-algae cultivation.

Another purpose of the present invention is to provide an instruction for the application of the carbon supply device in micro-algae cultivation.

The other purpose of the present invention is to provide use of the carbon supply device in micro-algae cultivation.

The carbon supply device for large scale cultivation of micro-algae according to the present invention includes a trap container, a partition plate, and a gas distributor.

The partition plate is installed vertically in the trap container and has a 10-50 cm gap from the container bottom, and the partition plate is higher than the wall of the trap container. The gas distributor is positioned at the bottom of the trap container.

A stirrer is provided at one side or both sides of the partition plate of the trap container.

The trap container has a width equal to that of the open pond; when the width is 40-500 cm, the depth is 30-300 cm, and the thickness is 20-200 cm.

The bottom of the trap container can be in the forms of flat, conic, or semicircular, and the trap container can be made from cement, plastic plate, stainless steel plate, brick, or the same material as that for the open pond.

The partition plate has a width matching with the trap container, and a thickness of 1.5-5 cm.

The partition plate can be made of plastic plate, stainless steel plate, or wood plate, which should be machinable, and has certain strength.

The partition plate can be positioned at the left (upstream side), middle, or right (downstream side) part of the trap container.

The distribution plate of the gas distributor is hydrophobic, and can be prepared from porous material such as glass sand core (hydrophobic), sieve with different meshes, and gauze, without restriction on shape. The number of the gas distributor is more than one.

The gas distributor can be positioned at left (upstream side), middle, or right (downstream side) part of the bottom of the trap container.

The main reason for the extremely low utilization of $CO_2$ during cultivation of micro-algae in open pond is the short gas-liquid contact time caused by the shallow culture solution. Therefore the $CO_2$ gas overflows without being absorbed sufficiently. The carbon supply device of the present invention is shown in FIG. 1, which overcomes the aforementioned disadvantage.

The application method of the carbon supply device for large scale cultivation of micro-algae according to the present invention is described as the followings: embedding the trap carbon supply device in the bottom of an open pond, wherein the upper end edge of the carbon supply device is aligned with the bottom of the open pond, and the middle partition plate is above the liquid level of the culture solution in the open pond such that the culture solution driven by a stirrer (the conventional stirrer adopted in the field) flows into the carbon supply device from one side of the device, passes through the bottom of the device, and flows out of the device from the other side of the device, leading to a greatly prolonged gas-liquid contact time. On the other hand, the gas distributor installed at the bottom of the carbon supply device converts carbon dioxide gas (or mixed gas containing carbon dioxide) passing through it into very small bubbles to sharply increase gas-liquid contact area; thus absorption of carbon dioxide is dramatically increased.

When the device is adopted in micro-algae cultivation, multiple trap carbon supply devices can be provided in the open pond. The number of the devices is determined according to carbon supplying rate of single carbon supply device, size of the open pond, growth rate of the object to be cultured and process requirement. The turbulence of the liquid can be achieved by stirrer used in conventional open ponds, such as impeller or mixing arm which are made from bamboo sheet, plastic, stainless steel, and other metal materials.

The flow rate of the culture solution in the trap carbon supply device is both in the range of 0.5-50 cm/s at the stage of flowing downwards and upwards. The flux of $CO_2$ gas (calculated as pure $CO_2$ at standard condition) at the bottom of the trap carbon supply device is 0.1-20 L/min per meter width.

The culture solution in the open pond has a depth of 1-20 cm. The supplied $CO_2$ can be cleaned flue gas, industrial $CO_2$ gas, pure $CO_2$ gas, air or other gases mixed with $CO_2$, or liquid $CO_2$.

The medium for micro-algae cultivation is any suitable medium for micro-algae growth and generally used in the field, such as Zarrouk medium, SM medium, $ASP_2$ medium, BG-11 medium, or medium satisfying special requirement of certain algae, as long as the cultivation requires $CO_2$.

The device according to the present invention is in the shape of trap, and can be used to supply $CO_2$ for large scale cultivation of various micro-algae in open pond, such as *Spirulina*, *Haematococcus pluvialis*, *Dunaliella salina*, *Chlorella*, or *Chlamydomonas Reinhardtii*.

According to the present invention, carbon dioxide can be effectively utilized to supply carbon for cultivating micro-algae in open pond, and the production cost can be greatly reduced. The invention has the following advantages:

(1) Utilization of carbon dioxide can be greatly improved, and $NaHCO_3$ can be replaced by carbon dioxide gas as the carbon source in micro-algae production, so the production cost is dramatically reduced.

(2) Desirable culture conditions is maintained by directly using $CO_2$ to avoid problems such as pH and salinity rise due to sodium carbonate accumulation caused by using $NaHCO_3$ as carbon source. Therefore, culture solution can be used repeatedly for an extended period, only nutrient salt required by algal cells needs to be supplemented in time to maintain appropriate concentration. The consumption of nutrient salt is greatly reduced.

(3) $CO_2$ is directly used as carbon source to allow water to be used repeatedly for an extended period. Carbon source and other nutrient salts can be automatically supplied, continuous or semi-continuous culture and harvest of micro-algae are easier to be achieved in the open pond, and large scale automatic production becomes easier.

(4) As continuous and semi-continuous culture and harvest of micro-algae in the open pond are achieved by directly using $CO_2$ as carbon source, the thickness (depth) of the culture solution can be reduced from 15-20 cm to 5 cm or lower (even 1 cm), as long as the horizontal level of the pond bottom is satisfactory during construction. Therefore the power for the culture mixing can be greatly reduced. Conventional stirrer (with stir manner and position as shown in FIG. 2) can be submerged into water to improve its stir efficiency (with stir manner and position as shown in FIG. 5), or combined with the carbon supply device (with stir manner and position as shown in FIGS. 3 and 4, in which the stirrer can be located at upstream side, downstream side, or both sides of the partition plate).

| Reference Signs | | |
|---|---|---|
| 1. Trap container | 2. Partition plate | 3. Gas distributor |
| 4. Actuator | 5. Stirrer | 6. Trap carbon supply device |
| 7. Gas distributor | 8. Flow meter | 9. Pressure gauge |
| 10. pH sensor | 11. Control unit | 12. $CO_2$ gas source |
| 13. Liquid level of micro-algae culture solution | | |

DETAILED DESCRIPTION OF THE PREFERRED EMBODIMENTS

Example 1

*Spirulina* is cultivated in a raceway pond which has perimeter of 200 m, width of 2 m, and water depth of 15 cm. The driving device for the culture solution is a steel impeller, and is driven by a motor. The algae, *Spirulina platensis*, are provided by Institute of Process Engineering, Chinese Academy of Sciences. The medium is Zarrouk medium, and the initial concentration of $NaHCO_3$ in the culture solution is 0.1 mol/L.

Figure 1:
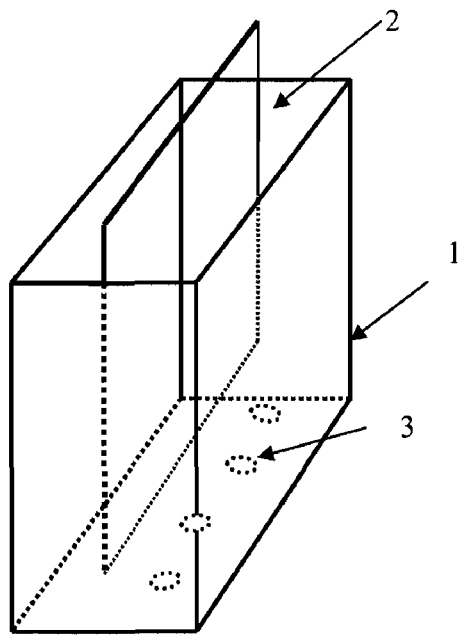
FIG. 1 shows the trap carbon supply device according to the present invention.
Figure 2:
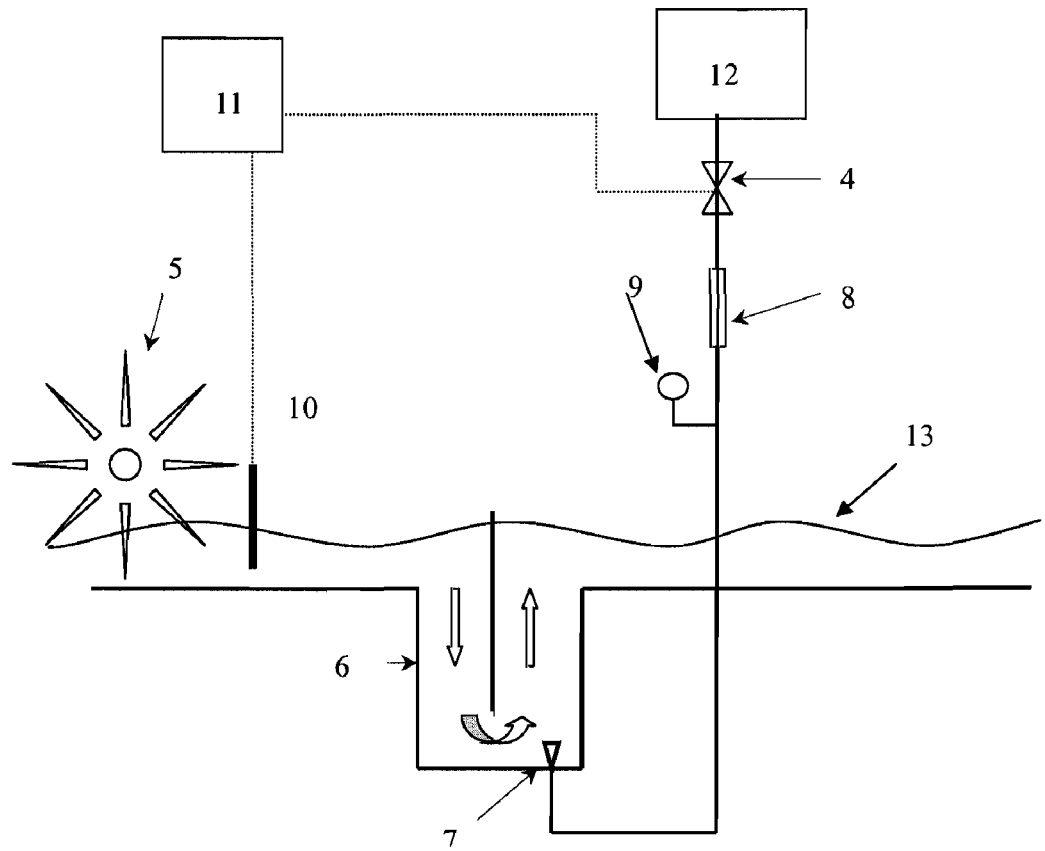
FIG. 2 shows the automatic carbon supply system using the trap carbon supply device according to the present invention.

Automatic carbon supplying is adopted, the automatic control method refers to CN200410009360.4 which is incorporated herein as reference, and the implementation system refers to FIG. 2, wherein pH sensor 10 is commercial pH electrode which can be sterilized by steam, control unit 11 is a pH meter with switch control, $CO_2$ gas source 12 is pure carbon dioxide gas, actuator 4 is two-position normally-closed solenoid valve (with diameter of 8 mm), and gas distributor 7 is glass sand core distributor plate (model G2). The carbon supply device has dimension as follows: the trap container has depth of 1 m, width of 2 m (equal to that of the raceway pond), and thickness of 20 cm. The trap container is made of cement (same as the material for culture pond, wherein the trap container is dug at the bottom of the culture pond). The partition plate is 1.5 cm-thick plastic plate, and located at middle along thickness direction, and has width matching with the trap container, wherein the lower end of the partition plate is 20 cm away from the bottom of the trap container. Four glass sand core gas distributors are installed in the bottom of the trap container, and at the downstream of the partition plate. The total number of carbon supply devices in the raceway pond is eight, the layout of each device is shown in FIG. 2, and the spaced intervals of each device are 25 m. Supplying of carbon dioxide is controlled according to the method in CN200410009360.4, i.e. carbon dioxide gas inlet valve is controlled to close or open according to pH of the culture solution. In this example, pH is controlled within 8.5-9.5. The flux (actuator 4 is open) of carbon dioxide gas in each trap container is 1.9 L/min (pure carbon dioxide, standard condition), and the liquid in the trap container flows upwards and downwards at a flow rate of 15 cm/s. When the density of algal cells reaches 1 g (dry weight)/L, semi-continuous harvest starts to harvest 20% of algal cells every three days by pumping out 20% of culture solution from the culture pond, filtering, returning to the cultivation pond, and washing and drying the harvested algal cells. The cultivation is carried out continuously for 2 months, during which concentration of other nutrient salts are analysed periodically and added in time, and small amount of water is supplemented to compensate water loss through evaporation. Unit area yield of algal cells reaches 10 g (dry weight)/$m^2$.d. The compositions of typical components, amino acids, fatty acids, and carotenoids of the obtained *Spirulina* powder are substantially consistent with those reported in the literatures. Carbon dioxide is consumed at 2.29 kg per kg algal powder (dry weight).

Example 2

This example is similar to example 1, except that the initial concentration of sodium bicarbonate is 0.2 mol/L, and the flux (actuator 4 is open) of carbon dioxide gas in each trap container is 4.0 L/min (standard condition). The cultivation is carried out continuously for 2 months, and the unit area yield of algae is 9.5 g/$m^2$.d. The compositions of typical components, amino acids, fatty acids, and carotenoids of the obtained *Spirulina* powder are substantially consistent with those reported in the literatures. Carbon dioxide is consumed at 2.62 kg per kg algal powder (dry weight).

Example 3

This example is similar to example 1, except that pH is controlled within 8.5-11.0, and the flux (actuator 4 is open) of carbon dioxide gas in each trap container is 4.0 L/min (standard condition). The cultivation is carried out continuously for 2 months, and the unit area yield of algae is 9.0 g/$m^2$.d. The compositions of typical components, amino acids, fatty acids, and carotenoids of the obtained *Spirulina* powder are substantially consistent with those reported in the literatures. Carbon dioxide is consumed at 2.5 kg per kg algal powder (dry weight).

Example 4

Figure 4:
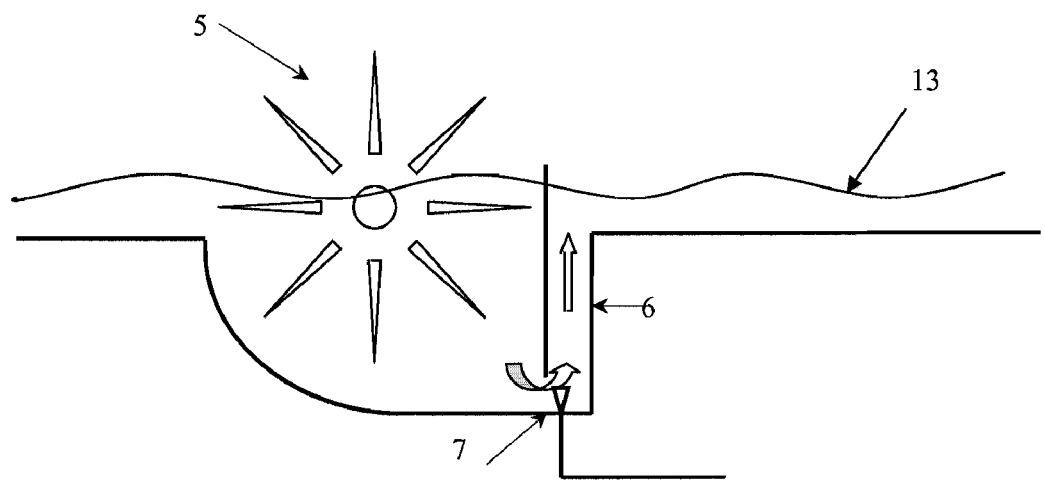
FIG. 4 shows the trap carbon supply device equipped with a stirrer at one side thereof according to the present invention, in which the stirrer has radius equivalent to the depth of the trap carbon supply device.

This example is similar to example 1, except that the structure of the trap carbon supply device is the structure as shown in FIG. 4. The trap container of the carbon supply device has depth of 50 cm and thickness of 55 cm; the partition plate is 10 cm away from the right wall (downstream side) of the trap container; and the gas distributor is right below the partition plate. ¼ circular groove with radius of 50 cm is dug at the side of the trap carbon supply device, the bottoms of the groove and the trap container are integrated, and the stirrer (with radius of 45 cm) is lowered to a position where the stir shaft is aligned with the liquid level to save stir power. The cultivation is carried out continuously for 2 months, and the unit area yield of algae is 10.2 g/$m^2$.d. The compositions of typical components, amino acids, fatty acids, and carotenoids of the obtained *Spirulina* powder are substantially consistent with those reported in the literatures. Carbon dioxide is consumed at 2.44 kg per kg algal powder (dry weight).

Example 5

This example is similar to example 1, except that the carbon supply device has width adjusted to 150 cm and depth of 50 cm; notch between the carbon supply device and the culture pond (with width of 2 m) is blocked; and three glass sand core gas distributors are installed at the bottom of each trap container. The cultivation is carried out continuously for 2 months, and the unit area yield of algae is 10.2 g/$m^2$.d. The compositions of typical components, amino acids, fatty acids, and carotenoids of the obtained *Spirulina* powder are substantially consistent with those reported in the literatures. Carbon dioxide is consumed at 2.35 kg per kg algal powder (dry weight).

Example 6

This example is similar to example 1, except that mixed gas of compressed air and carbon dioxide is introduced. The flux (actuator 4 is open) of the mixed gas containing 50% of carbon dioxide (molecular percentage) in each trap container is 3.8 L/min (standard condition). The cultivation is carried out continuously for 2 months, and the unit area yield of algae is 10.3 g/$m^2$.d. The compositions of typical components, amino acids, fatty acids, and carotenoids of the obtained *Spirulina* powder are substantially consistent with those reported in the literatures. Carbon dioxide is consumed at 2.62 kg per kg algal powder (dry weight).

Example 7

This example is similar to example 1, except that mixed gas of compressed air and carbon dioxide is introduced. The flux (actuator 4 is open) of the mixed gas containing 20% of carbon dioxide in each trap container is 6.0 L/min (standard condition), and pH is controlled within 9.0±0.2. The cultivation is carried out continuously for 2 months, and the unit area yield of algae is 12 g/m2.d. The compositions of the typical components, amino acids, fatty acids, and carotenoids of the obtained *Spirulina* powder are substantially consistent with those reported in the literatures. Carbon dioxide is consumed at 2.6 kg per kg algal powder (dry weight).

Example 8

This example is similar to example 1, except that the flux of carbon dioxide gas is 1.2 L/min (standard condition), and pH is controlled within 9.0±0.2. The cultivation is successful, and unit area yield of algae is 11.8 g/m$^2$.d. The compositions of the typical components, amino acids, fatty acids, and carotenoids of the obtained *Spirulina* powder are substantially consistent with those reported in the literatures. Carbon dioxide is consumed at 2.5 kg per kg algal powder (dry weight).

Example 9

This example is similar to example 1, except that pH is detected manually and carbon supplying is controlled manually. The cultivation is carried out continuously for 2 months, during which water and nutrient salt are supplemented. The unit area yield of algae within 2 months is 10.1 g (dry weight)/m$^2$.d. The compositions of the typical components, amino acids, fatty acids, and carotenoids of the obtained *Spirulina* powder are substantially consistent with those reported in the literatures. Carbon dioxide is consumed at 2.3 kg per kg algal powder (dry weight).

Example 10

This example is similar to example 1, except that the number of carbon supply devices is reduced to 4, and the devices are spaced at interval of 50 m. The flux (actuator 4 is open) of the carbon dioxide gas in each trap container is 3.0 L/min (standard condition). The cultivation is carried out for 2 months, and unit area yield of algae is 9.5 g/m$^2$.d. The compositions of the typical components, amino acids, fatty acids, and carotenoids of the obtained *Spirulina* powder are substantially consistent with those reported in the literatures. Carbon dioxide is consumed at 2.4 kg per kg algal powder (dry weight).

Example 11

This example is similar to example 1, except that the number of carbon supply devices is reduced to 4, and the devices are spaced at interval of 50 m. Mixed gas of compressed air and carbon dioxide is introduced. The flux (actuator 4 is open) of the mixed gas containing 20% (molecular percentage) of carbon dioxide in each trap container is 6.0 L/min (standard condition). The cultivation is carried out for 2 months, and unit area yield of algae is 9.5 g/m$^2$.d. The compositions of the typical components, amino acids, fatty acids, and carotenoids of the obtained *Spirulina* powder are substantially consistent with those reported in the literatures. Carbon dioxide is consumed at 3.05 kg per kg algal powder (dry weight).

Example 12

Figure 3:
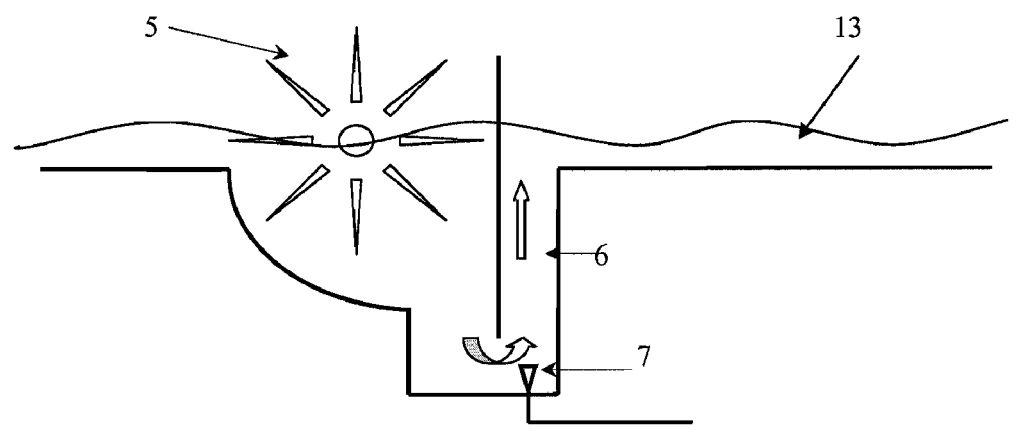
FIG. 3 shows the trap carbon supply device equipped with a stirrer at one side thereof according to the present invention, in which the stirrer has radius smaller than the depth of the trap carbon supply device.

This example is similar to example 1, except that the structure of the trap carbon supply device is the structure as shown in FIG. 3. The culture solution has depth of 5 cm; the trap container has thickness of 55 cm; the partition plate is 10 cm away from the right wall (downstream side) of the trap container; and the gas distributor is right below the partition plate. ¼ circular groove with radius of 50 cm is dug at the side of the trap carbon supply device, and the stirrer (with radius of 45 cm) is lowered to a position where the stir shaft is aligned with the liquid level to save stir power. The cultivation is carried out continuously for 2 months, 20% algal cells are harvested everyday, and the unit area yield of algae is 9.4 g/m$^2$.d. The compositions of the typical components, amino acids, fatty acids, and carotenoids of the obtained *Spirulina* powder are substantially consistent with those reported in the literatures. Carbon dioxide is consumed at 2.29 kg per kg algal powder (dry weight).

Example 13

Figure 5:
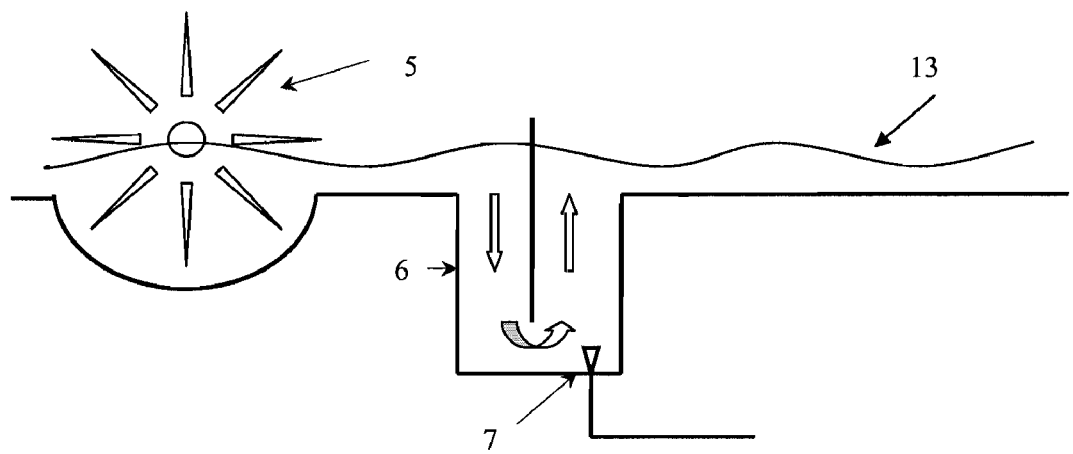
FIG. 5 shows the trap carbon supply device which is equipped with a matched semicircular container having stirrer.
Figure 6:
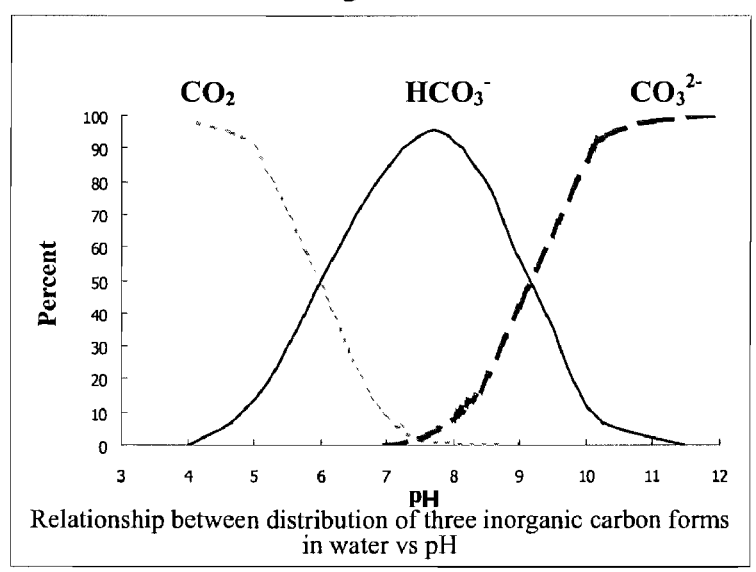
FIG. 6 is the graph showing the variation of pH along with inorganic carbon in the form of $HCO_3{-}$, $CO_3^{2-}$, and free $CO_2$ in micro-algal culture solution.

This example is similar to example 1, except that the structure of the trap carbon supply device is the structure as shown in FIG. 5; The culture solution has depth of 2 cm; and semicircular groove is dug under the stirrer, and the stirrer is lowered to a position where the stir shaft is aligned with the liquid level to save stir power. The cultivation is carried out continuously for 2 months, 50% algal cells are harvested everyday, and the unit area yield of algae is 9.4 g/m$^2$.d. The compositions of the typical components, amino acids, fatty acids, and carotenoids of the obtained *Spirulina* powder are substantially consistent with those reported in the literatures. Carbon dioxide is consumed at 2.3 kg per kg algal powder (dry weight).

What is claimed is:

1. An application method of a trap carbon supply device for large scale cultivation of micro-algae in an open pond, the trap carbon supply device comprising a trap container, a partition plate, and a gas distributor, wherein the partition plate is installed vertically in the trap container and has a 10-50 cm gap from a bottom of the container, the partition plate being higher than a wall of the trap container; and the gas distributor being positioned at the bottom of the trap container, the application method comprising embedding the trap carbon supply device in a bottom of the open pond, wherein an upper end edge of the trap carbon supply device is aligned with the bottom of the open pond, and the partition plate is above a liquid level of a culture solution in the open pond such that the culture solution driven by a stirrer flows into the trap carbon supply device from one side thereof, passes through the bottom thereof, and flows out of the device from another side thereof;

a flow rate of the culture solution in the trap carbon supply device is each 0.5-50 cm/s during flowing downwards and upwards; and a flux of $CO_2$ gas, calculated as pure $CO_2$ at standard condition, at the bottom of the trap carbon supply device is 0.1-20 L/min per meter width.

2. The method of claim 1, wherein a semicircular container with a stirrer is collocated with the trap carbon supply device and the semicircular container and the trap carbon supply device are applied together.

3. The method of claim 1, wherein the culture solution in the open pond has a depth of 1-20 cm.

4. The method of claim 1, wherein the $CO_2$ is cleaned flue gas, industrial $CO_2$ gas, pure $CO_2$ gas, air mixed with $CO_2$, or liquid $CO_2$.

5. The method of claim 1, wherein a stirrer is installed at one side or both sides of the partition plate of the trap container.

6. The method of claim 1, wherein the trap container has a width equal to that of the open pond.

7. The method of claim 6, wherein the trap container has a width of 40-500 cm, a depth of 30-300 cm, and a thickness of 20-200 cm.

8. The method of claim 6, wherein the bottom of the trap container is flat, conic, or semicircular.

9. The method of claim 5, wherein the trap container has a width equal to that of the open pond.

10. The method of claim 9, wherein the trap container has a width of 40-500 cm, a depth of 30-300 cm, and a thickness of 20-200 cm.

11. The method of claim 9, wherein the bottom of the trap container is flat, conic, or semicircular.

12. The method of claim 5, wherein the partition plate has a width matching with the trap container.

13. The method of claim 5, wherein the bottom of the trap container is flat, conic, or semicircular.

14. The method of claim 7, wherein the bottom of the trap container is flat, conic, or semicircular.

15. The method of claim 1, wherein the bottom of the trap container is flat, conic, or semicircular.

16. The method of claim 1, wherein the partition plate has a width matching with the trap container.

17. An application method of a trap carbon supply device for large scale cultivation of micro-algae in an open pond, the trap carbon supply device comprising a trap container, a partition plate, and a gas distributor, wherein the partition plate is installed vertically in the trap container and has a 10-50 cm gap from a container bottom, and the partition plate is higher than a wall of the trap container; the gas distributor is positioned at the bottom of the trap container; and a stirrer is installed at one or both sides of the partition plate of the trap container, the application method comprising embedding the trap carbon supply device in the bottom of the open pond, wherein an upper end edge of the carbon supply device is aligned with the bottom of the open pond, and the partition plate is above a liquid level of a culture solution in the open pond such that the culture solution driven by a stirrer flows into the trap carbon supply device from one side thereof, passes through the bottom thereof, and flows out of the device from another side thereof;
a flow rate of the culture solution in the trap carbon supply device is each 0.5-50 cm/s during flowing downwards and upwards; and
a flux of $CO_2$ gas, calculated as pure $CO_2$ at standard condition, at the bottom of the trap carbon supply device is 0.1-20 L/min per meter width.

18. An application method of a trap carbon supply device for large scale cultivation of micro-algae in an open pond, the trap carbon supply device comprising a trap container, a partition plate, and a gas distributor, wherein the partition plate is installed vertically in the trap container and has a 10-50 cm gap from a container bottom, and the partition plate is higher than a wall of the trap container; the gas distributor is positioned at the bottom of the trap container; and the trap container has a width equal to that of the open pond, the application method comprising embedding the trap carbon supply device in the bottom of the open pond, wherein an upper end edge of the trap carbon supply device is aligned with the bottom of the open pond, and the partition plate is above a liquid level of a culture solution in the open pond such that the culture solution driven by a stirrer flows into the trap carbon supply device from one side thereof, passes through the bottom thereof, and flows out of the device from another side thereof;
a flow rate of the culture solution in the trap carbon supply device is each 0.5-50 cm/s during flowing downwards and upwards; and
a flux of $CO_2$ gas, calculated as pure $CO_2$ at standard condition, at the bottom of the trap carbon supply device is 0.1-20 L/min per meter width.

19. An application method of a trap carbon supply device for large scale cultivation of micro-algae in an open pond, the trap carbon supply device comprising a trap container, a partition plate, and a gas distributor, wherein the partition plate is installed vertically in the trap container and has a 10-50 cm gap from a container bottom, and the partition plate is higher than a wall of the trap container; the gas distributor being positioned at the bottom of the trap container; the trap container has a width equal to that of the open pond; and the trap container has a width of 40-500 cm, a depth of 30-300 cm, and a thickness of 20-200 cm,
the application method comprising embedding the trap carbon supply device in a bottom of the open pond, wherein an upper end edge of the trap carbon supply device is aligned with the bottom of the open pond, and the partition plate is above a liquid level of a culture solution in the open pond such that the culture solution driven by a stirrer flows into the trap carbon supply device from one side thereof, passes through the bottom thereof, and flows out of the device from another side thereof;
the flow rate of the culture solution in the trap carbon supply device is each 0.5-50 cm/s during flowing downwards and upwards; and
the flux of $CO_2$ gas, calculated as pure $CO_2$ at standard condition, at the bottom of the trap carbon supply device is 0.1-20 L/min per meter width.

20. An application method of a trap carbon supply device for large scale cultivation of micro-algae in an open pond, the trap carbon supply device comprising a trap container, a partition plate, and a gas distributor, wherein the partition plate is installed vertically in the trap container and has a 10-50 cm gap from a container bottom, and the partition plate is higher than a wall of the trap container; the gas distributor is positioned at the bottom of the trap container; and the bottom of the trap container is flat, conic, or semicircular,
the application method comprising embedding the trap carbon supply device in the bottom of the open pond, wherein the upper end edge of the trap carbon supply device is aligned with the bottom of the open pond, and the partition plate is above a liquid level of a culture solution in the open pond such that the culture solution driven by a stirrer flows into the trap carbon supply device from one side thereof, passes through the bottom thereof, and flows out of the device from another side thereof;
a flow rate of the culture solution in the trap carbon supply device is each 0.5-50 cm/s during flowing downwards and upwards; and
a flux of $CO_2$ gas, calculated as pure $CO_2$ at standard condition, at the bottom of the trap carbon supply device is 0.1-20 L/min per meter width.

* * * * *